(12) United States Patent
Flanders et al.

(10) Patent No.: US 6,686,170 B1
(45) Date of Patent: Feb. 3, 2004

(54) ASSAY DEVICES WITH MOBILE CONTROL REAGENTS

(75) Inventors: Richard T. Flanders, Grayslake, IL (US); Vincent A. Varitek, Jr., Wildwood, IL (US)

(73) Assignee: Abbott Laboratories, Abbott Park, IL (US)

( * ) Notice: Subject to any disclaimer, the term of this patent is extended or adjusted under 35 U.S.C. 154(b) by 1,575 days.

(21) Appl. No.: 08/292,157

(22) Filed: Aug. 17, 1994

(51) Int. Cl.⁷ .................. G01N 33/569; G01N 33/53; C12Q 1/00; A61K 39/40
(52) U.S. Cl. .............. 435/7.34; 435/4; 435/962; 435/967; 436/531; 436/8; 436/169
(58) Field of Search .................. 422/55, 56, 57, 422/61, 119; 435/4, 7.1, 7.34, 7.9, 7.92, 7.93, 7.94, 7.95, 805, 806, 810, 962, 967, 970, 971; 436/510, 514, 518, 523, 528, 531, 533, 534, 8, 60, 163, 810, 814, 906

(56) References Cited

U.S. PATENT DOCUMENTS

| | | | |
|---|---|---|---|
| 4,157,280 A | * 6/1979 | Halbert et al. ............. 195/127 |
| 4,361,537 A | 11/1982 | Deutsch et al. |
| 4,446,232 A | 5/1984 | Liotta |
| 4,826,759 A | 5/1989 | Guire et al. |
| 4,956,302 A | 9/1990 | Gordon et al. |
| 5,075,078 A | * 12/1991 | Osikowicz et al. ............. 422/56 |
| 5,081,013 A | 1/1992 | Rovelli et al. |
| 5,156,953 A | 10/1992 | Litman et al. |
| 5,160,701 A | 11/1992 | Brown, III et al. |
| 5,356,782 A | * 10/1994 | Moorman et al. ............. 435/7.9 |

FOREIGN PATENT DOCUMENTS

| EP | 0389003 | 9/1990 |
|---|---|---|
| EP | 056040411 | 9/1993 |
| WO | 9502822 | 1/1995 |

OTHER PUBLICATIONS

Hybritech Incorporated, "ICONII® HCG", published Feb. 1992.
Kodak Clinical Products, "SURECELL® HcG–Urine Test Kit", published May, 1991.
Wampole/Unipath, Ltd., "Clearview Strep A", from manufacturer's package insert.

* cited by examiner

*Primary Examiner*—Yvonne Eyler
(74) *Attorney, Agent, or Firm*—Regina M. Anderson

(57) ABSTRACT

The present invention relates to an improved immunoassay device for confirming the validity of a test result showing either the presence or absence of an analyte in a patient sample. In the improved device, control reagents are provided in the device which directly mimic the reaction of the sample analyte with the test reagents of the device. The device thus allows the user to verify the efficacy of the test reagents at all stages of interaction with the sample analyte.

13 Claims, 1 Drawing Sheet

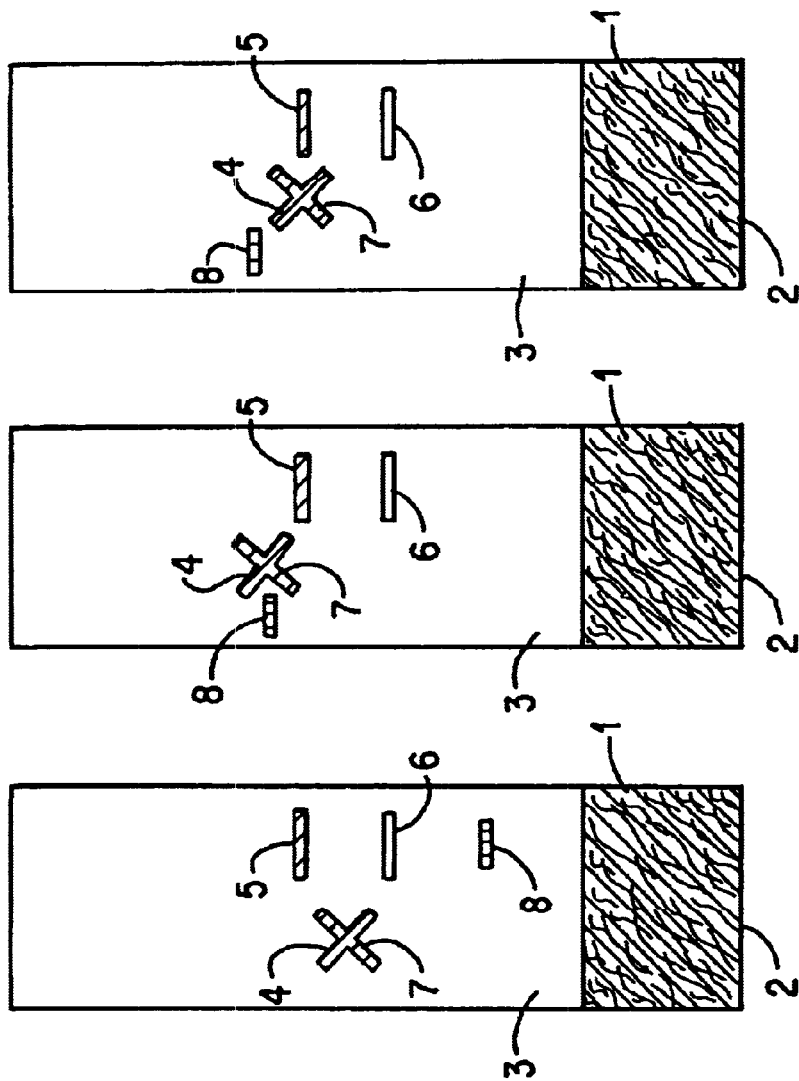
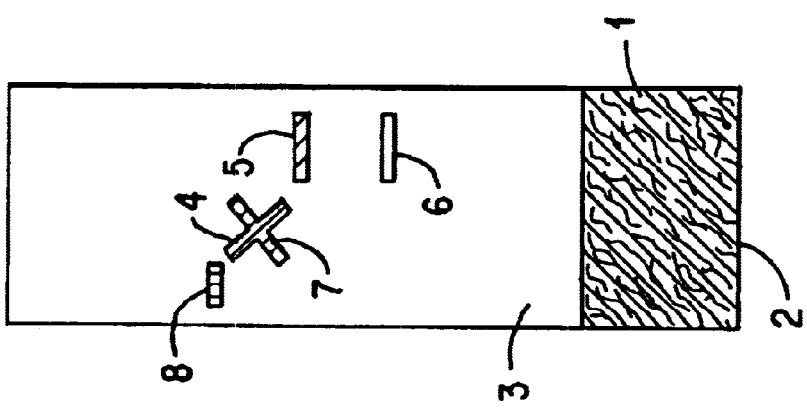

ASSAY DEVICES WITH MOBILE CONTROL REAGENTS

BACKGROUND OF THE INVENTION

1. Field of the Invention

The present invention relates to a novel test device for detecting an analyte in a test sample by means of a binding assay. In particular, this invention relates to a novel test device incorporating mobile control reagents.

2. Description of Related Art

The ability to use materials which specifically bind to an analyte of interest has provided a means for developing diagnostic devices based on the use of binding assays. Binding assays incorporate specific binding members, typified by antibody and antigen immunoreactants, wherein one member of the specific binding pair is labeled with a signal-producing compound (e.g., an antibody labeled with an enzyme, a fluorescent compound, a chemiluminescent compound, a radioactive isotope, a direct visual label, etc.). For example, in a binding assay the test sample suspected of containing analyte can be mixed with a labeled reagent, e.g., labeled anti-analyte antibody, and incubated for a period of time sufficient for the immunoreaction to occur. The reaction mixture is subsequently analyzed to detect either that label which is associated with an analyte/labeled reagent complex (bound labeled reagent) or that label which is not complexed with analyte (free labeled reagent). As a result, the amount of free or bound label can be correlated to the amount of analyte in the test sample.

The solid phase assay format is a commonly used binding assay technique. There are a number of assay devices and procedures wherein the presence of an analyte is indicated by the analyte's capacity to bind to a labeled reagent and an immobilized or insoluble complementary binding member. The immobilized binding member is bound, or becomes bound during the assay, to a solid phase such as a dipstick, teststrip, flow-through pad, paper, fiber matrix or other suitable solid phase material. The binding reaction between the analyte and the assay reagents results in a partitioning of the labeled reagent between that which is immobilized upon the solid phase and that which remains free. The presence or amount of analyte in a test sample is typically indicated by the extent to which the labeled reagent becomes immobilized upon the solid phase material.

The use of reagent-impregnated teststrips in specific binding assays is well-known. (See, eg. Deutsch, et al. U.S. Pat. No. 4,361,537, and Brown, III et al. U.S. Pat. No. 5,160,701). In such procedures, a test sample is applied to one portion of the teststrip and is allowed to migrate or wick through the strip material. Thus, the analyte to be detected or measured passes through or along the material, possibly with the aid of an eluting solvent which can be the test sample itself or a separately added solution. The analyte migrates into or through a capture or detection zone on the teststrip, wherein a complementary binding member to the analyte is immobilized. The extent to which the analyte becomes bound in the detection zone can be determined with the aid of the labeled reagent which can also be incorporated in the teststrip or which can be applied separately.

In general, teststrips involve a material capable of transporting a solution by capillary action, i.e., a wicking or chromatographic action as exemplified in Gordon et al. U.S. Pat. No. 4,956,302. Different areas or zones in the teststrip contain the assay reagents needed to produce a detectable signal as the analyte is transported to or through such zones. The device is suited for both chemical assays and binding assays and uses a developer solution to transport analyte along the strip.

To verify the stability and the efficacy of the assay reagents needed to produce the detectable signal, existing assays typically require that one or more strips from each manufacturing lot be separately assayed for both positive and negative controls. For the positive control, this typically requires a solution 'spiked' with the analyte of interest which is applied to the strip and developed as described above. A negative control will use a 'blank' sample, that is, one which has no analyte present. However, these methods require the use of separate strips which are not controlling for device specific variations in procedure or reagents, and are not developed under the actual assay conditions, i.e., in the presence of a patient sample. Furthermore, the need for parallel testing of controls significantly increases the cost of performing diagnostic assays.

Another disadvantage of conventional teststrip devices having control reagents is that the controls fail to exactly mimic the reaction of a patient sample with the teststrip reagents. For example, in teststrip devices utilizing a sandwich assay format, an analyte is first reacted with a labeled binding reagent to form a complex which then becomes bound to a detection site on the device via a second binding reagent. Although certain control reagents provided in these devices control for one portion of the total patient sample reaction, such as the binding of labeled reagent to the analyte, no control is provided to verify the second portion of the patient sample reaction, i.e. the binding of the labeled complex to the binding reagent at the detection site. The failure of either of these binding reactions to occur leads to the erroneous conclusion of a negative patient sample. Thus, there is a need for specific control reagents which permit the simultaneous confirmation of the assay results by mimicking the entire patient reaction.

SUMMARY OF THE INVENTION

The invention provides, in an analytical device for determining the presence or amount of an analyte in a test sample, having a strip with a proximal end and a distal end, wherein the test sample can travel from the proximal end to about the distal end by capillary action, and wherein the strip contains an immobilized patient capture reagent which binds to a member selected from the group consisting of the analyte, an ancillary specific binding member and a labeled reagent, the improvement comprising:
  a) a mobile positive control reagent;
  b) an immobilized positive control capture reagent that is located downstream from the mobile positive control reagent and is capable of binding the mobile positive control reagent.

The invention also provides an immobilized negative control reagent used to determine the presence of non-specific binding or aggregation of any labeled reagent in the device at a site independent of the positive control reagent and positive control capture reagent.

The test kits of the present invention contain the analytical device and may include additional instructions and/or ancillary reagents such as diluents and buffers.

BRIEF DESCRIPTION OF THE FIGURES

FIG. 1 is a top view of a test strip device of the present invention having control means configured on the strip.

FIG. 2 shows alternate configurations for the device shown in FIG. 1.

DETAILED DESCRIPTION OF THE INVENTION

Before proceeding with the description of the various embodiments of the present invention, a number of terms used herein will be defined.

I. DEFINITIONS

"Test sample" refers to a material suspected of containing the analyte. The test sample can be used directly as obtained from the source or after pretreatment so as to modify its character. The test sample can be derived from any source, such as a physiological fluid, including, plasma or serum from blood, saliva, ocular lens fluid, cerebral spinal fluid, sweat, urine, milk, ascites fluid, mucous, synovial fluid, peritoneal fluid, amniotic fluid or the like. The test sample can be pretreated prior to use, such as preparing plasma from blood, diluting viscous fluids, or the like; methods of treatment can involve extraction, filtration, distillation, concentration, inactivation of interfering components, and the addition of reagents. Besides physiological fluids, other liquid samples can be used such as water, food products and the like for the performance of environmental or food production assays as well as diagnostic assays. In addition, a solid material suspected of containing the analyte can be used as the test sample once it is modified to form a liquid medium or to release the analyte.

"Specific binding member" refers to a member of a specific binding pair, i.e., two different molecules wherein one of the molecules specifically binds to the second molecule through chemical or physical means. In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog or a specific binding member made by recombinant techniques or molecular engineering. If the specific binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other specific binding members. The details of the preparation of such antibodies and their suitability for use as specific binding members are well-known to those skilled-in-the-art.

"Analyte" or "analyte of interest" refers to the compound or composition to be detected or measured, which has at least one epitope or binding site. The analyte can be any substance for which there exists a naturally occurring analyte-specific binding member or for which an analyte-specific binding member can be prepared. Analytes include, but are not limited to toxins, organic compounds, proteins, peptides, microorganisms, amino acids, nucleic acids, hormones, steroids, vitamins, drugs (including those administered for therapeutic purposes as well as those administered for illicit purposes), and metabolites of or antibodies to any of the above substances. The term "analyte" also includes any antigenic substances, haptens, antibodies, macromolecules and combinations thereof.

"Analyte-analog" refers to a substance which cross-reacts with the analytespecific binding member, although it may do so to a greater or a lesser extent than does the analyte itself. The analyte-analog can include a modified analyte as well as a fragmented or synthetic portion of the analyte molecule, so long as the analyte-analog has at least one epitopic site in common with the analyte of interest. An example of an analyte-analog is a synthetic peptide sequence which duplicates at least one epitope of the whole-molecule analyte so that the analyte-analog can bind to the analytespecific binding member.

"Positive control reagent" refers to a reagent that mimics the reaction between the test analyte of interest and the teststrip reagents. Specifically a positive control reagent refers to a mobile specific binding member that is related to the analyte of interest and whose binding specificity mimics that of the analyte. Thus the positive control reagent may be either an analyte identical to that of the test sample or a corresponding analyte-analog which is capable of specifically binding both to the labeled reagent and/or to the positive control capture reagent.

"Confirmatory assay" refers to any control means located on the teststrip which verifies the test reagents of the device. A control means may be any reagent or combination of reagents which, having operated in accordance with the method of the device, serves as an indicator to the user that the test reagents have functioned properly and that the test results are valid. For example, a control means may be either a negative control reagent, or the combination of positive control reagent and positive control capture reagent. Multiple confirmatory reagents may also be present on a single device.

"Labeled reagent" refers to a substance comprising a detectable label attached to a specific binding member. The attachment may be covalent or non-covalent binding, but the method of attachment is not critical to the present invention. The label allows the labeled reagent to produce a detectable signal that is directly or indirectly related to the amount of analyte in the test sample. The specific binding member component of the labeled reagent is selected to directly bind to the analyte or to indirectly bind the analyte by means of an ancillary specific binding member, which is described in greater detail hereinafter. The labeled reagent can be incorporated into the test device, it can be combined with the test sample to form a test solution, it can be added to the device separately from the test sample or it can be predeposited or reversibly immobilized at the capture site. In addition, the binding member may be labeled before or during the performance of the assay by means of a suitable attachment method.

"Label" refers to any substance which is capable of producing a signal that is detectable by visual or instrumental means. Various labels suitable for use in the present invention include labels which produce signals through either chemical or physical means. Such labels can include enzymes and substrates; chromogens; catalysts; fluorescent compounds; chemiluminescent compounds; radioactive labels; direct visual labels including colloidal metallic particles such as gold, colloidal nonmetallic particles such as selenium, dyed or colored particles such as a dyed plastic or a stained microorganism, colored or colorable organic polymer latex particles, and liposomes or other vesicles containing directly visible substances; and the like.

The selection of a particular label is not critical to the present invention, but the label will be capable of generating a detectable signal either by itself, such as a visually detectable colored organic polymer latex particle or instrumentally detectable, such as a fluorescent compound, or detectable in conjunction with one or more additional signal producing components, such as an enzyme/substrate signal producing system. A variety of different labeled reagents can be formed by varying either the label or the specific binding member component of the labeled reagent; it will be appreciated by one skilled-in-the-art that the choice involves consideration of the analyte to be detected and the desired means of detection.

When using a visually detectable particle as the label, such as selenium, dyed particles or black latex, the labeled reagent binding member and the control reagent binding member may both be attached to the particles. Alternatively, the binding members may be attached to separate batches of particles and the particles are then mixed.

"Signal producing component" refers to any substance capable of reacting with another assay reagent or with the analyte to produce a reaction product or signal that indicates the presence of the analyte and/or serves to indicate that certain assay characteristics have been satisfied. The signal producing component is detectable by visual or instrumental means. "Signal production system", as used herein, refers to the group of assay reagents that are needed to produce the desired reaction product or signal. For example, one or more signal producing components can be reacted with the label to generate a detectable signal, e.g., when the label is an enzyme, amplification of the detectable signal is obtained by reacting the enzyme with one or more substrates or additional enzymes and substrates to produce a detectable reaction product.

In a preferred embodiment of the present invention, a visually detectable label is used as the label component of the labeled reagent, thereby providing for the direct visual or instrumental readout of the presence or amount of the analyte in the test sample without the need for additional signal producing components at the detection sites. Suitable materials for use include colloidal metals, such as gold, and dye particles. Non-metallic colloids, such as colloidal selenium, tellurium and sulfur particles may also be used. In an alternate preferred embodiment, a visually detectable label is used as just described and additional signal producing components are present which, when reacted with the visually detectable label, serve as both positive and negative control indicators.

"Immobilized capture reagent" refers to one or more specific binding members that are attached within or upon a portion of the solid phase support or chromatographic strip to form one or more "capture sites" wherein the analyte, positive control reagent, and/or labeled reagent become immobilized on the strip or wherein the immobilized reagent slows the migration of the analyte and/or labeled reagent through the strip. The method of attachment is not critical to the present invention. The immobilized capture reagent facilitates the observation of the detectable signal by substantially separating the analyte and/or the labeled reagent from unbound assay reagents and the remaining components of the test sample. In addition, the immobilized reagent may be immobilized on the solid phase before or during the performance of the assay by means of any suitable attachment method.

Typically, a capture site of the present invention is a delimited or defined portion of the solid phase support such that the specific binding reaction between the immobilized capture reagent and analyte and/or the immobilized capture reagent and positive control reagent is localized or concentrated in a delimited site. This facilitates the detection of label that is immobilized at the capture site or sites in contrast to other portions of the solid phase support. The delimited site is typically less than 50% of the solid phase support, and preferably less than 10% of the solid phase support. The immobilized reagent can be applied to the solid phase material by dipping, inscribing with a pen, dispensing through a capillary tube or through the use of reagent jet-printing or any other suitable dispensing techniques. In addition, the capture site can be marked, for example with a dye, such that the position of the capture site upon the solid phase material can be visually or instrumentally determined even when there is no label immobilized at the site. Preferably, the immobilized reagent is positioned on the strip such that the capture site is not directly contacted with the test sample, that is, the test sample must migrate by capillary action through at least a portion of the strip before contacting the immobilized reagent.

The immobilized capture reagent may be provided in a single capture or detection site or in multiple sites on or in the solid phase material. The preferred embodiment of the invention provides for an immobilized positive control capture reagent, an immobilized patient capture reagent and an immobilized procedural capture reagent. The immobilized capture reagents may also be provided in a variety of configurations to produce different detection or measurement formats. For example, the immobilized capture reagent may be configured as a letter, number, icon or symbol or any combination thereof. When configured as a letter, the immobilized capture reagent may be either a single letter or combination of letters that form words or abbreviated words such as "POS", "NEG" or "OK". Alternatively, the immobilized capture reagent may be configured as a symbol or combination of symbols, such as for example, a plus, minus, check-mark, bar, diamond, triangle, rectangle, circle, oval, square, arrow, line or any combination thereof. Alternatively, the immobilized reagent can be distributed over a large portion of the solid phase material in a substantially uniform manner to form the capture site. The extent of signal production in the patient capture site is related to the amount of analyte in the test sample, whereas the extent of signal production in the positive control capture site is related both to the amount of positive control reagent applied to the strip and to the amount of analyte present in the test sample. That is, in the absence of sample analyte, the signal production at the positive control capture site will result exclusively from binding of the positive control reagent, whereas, in the presence of sample analyte, some proportion of the signal generated may result from the binding of the analyte, in addition to the binding of the positive control reagent.

"Negative binding reagent" refers to any substance which is immobilized on the teststrip at a site distinct and independent from the immobilized capture reagents and which is used to determine the presence of non-specific binding or aggregation of any labeled reagent. The immobilized negative control reagent may be, for example, a substance comprising specific binding members such as antigens, antibodies or antibody fragments. Additionally, the negative control reagent may be derived from the same or a different species as the other reagents on the teststrip or from a combination of two or more species. The presence of a detectable signal at the position of the negative control reagent on the teststrip indicates an invalid test.

"Ancillary specific binding member" refers to any member of a specific binding pair which is used in the assay in addition to the specific binding members of the labeled reagent or immobilized reagent. One or more ancillary specific binding members can be used in an assay. For example, an ancillary specific binding member can be capable of binding the labeled reagent to the analyte of interest, in instances where the analyte itself could not directly attach to the labeled reagent. Alternatively, an ancillary specific binding member can be capable of binding the immobilized reagent to the analyte of interest, in instances where the analyte itself could not directly attach to the immobilized reagent. The ancillary specific binding member can be incorporated into the assay device or it can be added to the device as a separate reagent solution.

II. DEVICE COMPONENTS

A. Strip

"Solid phase support" or "chromatographic material" or "strip" refers to any suitable porous, absorbent, bibulous, isotropic or capillary material, which includes the reaction site of the device and through which the analyte or test sample can be transported by a capillary or wicking action. It will be appreciated by one skilled-in-the-art that the strip can be made of a single material or more than one material (e.g., different zones, portions, layers, areas or sites can be made of different materials) so long as the multiple materials are in fluid-flow contact with one another thereby enabling the passage of test sample between the materials.

Fluid-flow contact permits the passage of at least some components of the test sample, e.g., analyte, between the zones of the porous material and is preferably uniform along the contact interface between the different zones.

Natural, synthetic, or naturally occurring materials that are synthetically modified, can be used as the solid-phase support and include, but are not limited to: papers (fibrous) or membranes (microporous) of cellulose materials such as paper, cellulose, and cellulose derivatives such as cellulose acetate and nitrocellulose; fiberglass; cloth, both naturally occurring (e.g., cotton) and synthetic (e.g., nylon); porous gels; and the like. The porous material should not interfere with the production of a detectable signal. The chromatographic material may have an inherent strength, or strength can be provided by means of a supplemental support.

The particular dimensions of the strip material will be a matter of convenience, depending upon the size of the test sample involved, the assay protocol, the means for detecting and measuring the signal, and the like. For example, the dimensions may be chosen to regulate the rate of fluid migration as well as the amount of test sample to be imbibed by the chromatographic material.

When appropriate, it is necessary to select strip dimensions which allow the combination of multiple strips in a single assay device. It is also within the scope of this invention to have a reagent, at the distal end of the chromatographic material, which indicates the completion of a binding assay (i.e., end of assay indicator) by changing color upon contact with the test solution, wicking solution or a signal producing component. Reagents which would change color upon contact with a test solution containing water are the dehydrated transition metal salts, such as $CuSO_4$, $Co(NO_3)_2$, and the like. The pH indicator dyes can also be selected to respond to the pH of the buffered wicking solution. For example, phenolphthalein changes from clear to intense pink upon contact with a wicking solution having a pH range between 8.0–10.0.

In a preferred embodiment one or more controls is provided on each of the strips. In addition, the location of the control capture sites relative to the patient capture site is such that the results of the reaction at the control capture sites are visually apparent either before, at the same time or later than the appearance of the assay result at the patient capture site. The binding of a mobile control reagent to its corresponding immobilized capture site or bar demonstrates that the assay reagents were reactive and that the assay reactions took place as planned.

The positive control reagent involves a specific binding member that is either an analyte identical to or an analyte-analog of the test analyte of interest. The positive control reagent is applied diffusively in a zone or site directly upstream of the positive control capture site. During the course of, for example, a sandwich assay, the patient sample is contacted with an application pad to which a labeled antianalyte reagent has been applied. The labeled antianalyte reagent is reconstituted and forms a complex with analyte present in the test sample. In either the presence or absence of analyte however, unbound labeled reagent migrates through the teststrip where it contacts the positive control reagent. The unbound labeled reagent and positive control reagent react to form a complex which then migrates to and becomes immobilized at the positive control capture site. A detectable signal is formed at the positive control capture site so that the user is assured both of the efficacy and viability of the assay reagents in either the absence or presence of signal at the patient capture site (indicating negative and positive results, respectively). Additionally, where an amount of capture reagent has been applied to the solid phase so as to effect capture of a specified amount of positive control reagent, the detectable signal formed can act as a reference standard for detectable signal generated at the patient or another or other capture sites, thereby permitting quantitation or semiquantitation of the assay results. The absence of a signal at the positive control capture site is indicative of a nonfunctional or invalid test.

It should be recognized that the positive control reagent may be employed for any type of immunological detection reaction, such as sandwich, immunometric and competitive assays or for indirect detection of antibodies. Where the type of reaction is such that the presence of analyte in a patient sample produces a lack of or reduction in signal at the patient capture site, (as with competitive and immunometric assays), the control reagent(s) may also be configured to mimic that reaction, for example, by producing a reduced signal at the positive control capture site. The control means thus serves, as in the sandwich assay format, to validate the result of the reaction between the sample analyte and reagents. To assist the user in understanding the results with such a true positive control, other control means may be utilized on the device. For example, it may be particularly useful in this situation to employ another control means to validate the integrity of the labeled reagent itself.

Capture reagents may be located anywhere along the teststrip in single or multiple pathways with the proviso that they be located in the fluid flow path of their respective labeled reagents. It is understood by those skilled in the art that as fluid migrates through the strip there is little cross flow of fluid. Thus, all mobile reagents coming into contact with the fluid also migrate in the direction of the fluid flow, i.e. there is no substantial migration of reagents transversely across the strip. A further proviso to the location of the capture reagents is that the patient capture site and the positive control capture site not lie downstream of each other on the teststrip. Areas of other controls can lie either adjacent, downstream or upstream to each other.

The present invention further provides kits for carrying out binding assays. For example, a kit according to the present invention can comprise the comb-type or card-type device with its incorporated reagents as well as a transport solution and/or test sample pretreatment reagent as described above. Other assay components known to those skilled in the art, include buffers, stabilizers, detergents, bacteria inhibiting agents and the like which can also be present in the assay device or separate reagent solution.

The present invention optionally includes a non reactive cover or enclosure around the device. Preferably, the cover encloses at least the strip to avoid contact with and contamination of the capture sites. The cover may also include a raised area adjacent to the application pad to facilitate receiving and/or containing a certain volume of the test sample and/or wicking solution. Additionally, the cover may include a cut out area or areas in the form of a letter, number, icon, or symbol or any combination thereof. In this embodiment, the cut out area or areas form the design for particular capture site or sites once the strip is completely enclosed. It is preferred that a sufficient portion of the strip be encased to prevent applied test sample from contacting the capture sites without first passing through a portion of the strip.

B. Application Pad

An optional device component is a test sample application pad. The application pad is in fluid flow contact with one end of the strip material, referred to as the proximal end, such that the test sample can pass or migrate from the application pad to the strip. Fluid flow contact can include physical contact of the application pad to the chromatographic material as well as the separation of the pad from the strip by an intervening space or additional material which still allows fluid to pass between the pad and the strip. Substantially all of the application pad can overlap the chromatographic material to enable the test sample to pass through substantially any part of the application pad to the proximal end of the strip. Alternatively, only a portion of the application pad might be in fluid flow contact with the chromatographic material. The application pad can be any material which can transfer the test sample to the chromatographic material and which can absorb a volume of test sample that is equal to or greater than the total volume capacity of the chromatographic material.

Materials preferred for use in the application pad include nitrocellulose, porous polyethylene frit or pads and glass fiber filter paper. The material must also be chosen for its compatibility with the analyte and assay reagents, for example, glass fiber filter paper was found to be the preferred application pad material for use in a human chorionic gonadotropin (hCG) assay device.

In addition, the application pad typically contains one or more assay reagents either diffusively or non-diffusively attached thereto. Reagents which can be contained in the application pad include, but are not limited to, labeled reagents, ancillary specific binding members, and signal producing system components needed to produce a detectable signal. For example, in a binding assay it is preferred that the labeled reagent be contained in the application pad. The labeled reagent is released from the pad to the strip with the application,of the test sample, thereby eliminating the need to combine the test sample and labeled reagent prior to using the device. The isolation of assay reagents in the application pad also keeps interactive reagents separate and facilitates the manufacturing process.

In some instances, the application pad also serves the function of an initial mixing site and a reaction site for the test sample and reagent. In preferred embodiments, the application pad material is selected to absorb the test sample at a rate that is faster than that achieved by the strip material alone. Typically, the pad material is selected to absorb fluids 2 to 5 times faster than the strip material. Preferably, the pad will absorb fluids 4 to 5 times faster than will the strip material.

In an optional embodiment of the present invention, gelatin is used to encompass all or part of the application pad. Typically, such encapsulation is produced by overcoating the application pad with fish gelatin. The effect of this overcoating is to increase the stability of the reagent contained by the application pad. The application of test sample to the overcoated application pad causes the gelatin to dissolve and thereby enables the dissolution of the reagent. In an alternative embodiment of the present invention, the reagent containing application pad is dried or lyophilized to increase the shelf-life of the device. Lyophilized application pads were found to produce stronger signals than air dried application pads, and the lyophilized application pads maintained stability for longer periods. The reagents contained in the application pad are rehydrated with the addition of test sample to the pad.

The present invention can be further modified by the addition of a filtration means. The filtration means can be a separate material placed above the application pad or between the application pad and the strip material, or the material of the application pad itself can be chosen for its filtration capabilities. The filtration means can include any filter or trapping device used to remove particles above a certain size from the test sample. For example, the filter means can be used to remove red blood cells from a sample of whole blood, such that plasma is the fluid received by the application pad and transferred to the chromatographic material.

Yet another modification of the present invention involves the use of an additional layer or layers of porous material placed between the application pad and the chromatographic material or overlaying the application pad. Such an additional pad or layer can serve as a means to control the rate of flow of the test sample from the application pad to the strip. Such flow regulation is preferred when an extended incubation period is desired for the reaction of the test sample and the reagent(s) in the application pad. Alternatively, such a layer can contain an additional assay reagent(s) which is preferably isolated from the application pad reagents until the test sample is added, or it can serve to prevent unreacted assay reagents from passing to the chromatographic material.

When small quantities of non-aqueous or viscous test samples are applied to the application pad, it may be necessary to employ a wicking or transport solution, preferably a buffered solution, to carry the reagent(s) and test sample from the application pad and through the strip. When an aqueous test sample is used, a transport solution generally is not necessary but can be used to improve flow characteristics through the device or to adjust the pH of the test sample. The transport solution typically has a pH range from about 5.5 to about 10.5, and more preferably from about 6.5 to about 9.5. The pH is selected to maintain a significant level of binding affinity between the specific binding members in a binding assay. When the label component of the indicator reagent is an enzyme, however, the pH also must be selected to maintain significant enzyme activity for color development in enzymatic signal production systems. Illustrative buffers include phosphate, carbonate, barbital, diethylamine, tris(hydromethyl)aminomethane (Tris), Bis-Tris, 2-amino-2-methyl-l-propanol and the like. The transport solution and the test sample can be combined prior to contacting the application pad or they can be contacted to the application pad sequentially.

Predetermined amounts of signal producing components and ancillary reagents can be incorporated within the device, thereby avoiding the need for additional protocol steps or reagent additions. Thus, it is also within the scope of this invention to provide more than one reagent to be immobilized within the application pad and/or the strip material.

III. PREFERRED EMBODIMENTS

This invention provides assay devices and methods, where the devices use strips of chromatographic material capable of transporting liquids for the performance of an assay on a patient sample or the performance of a multiple assay on a patient sample. The device may include test sample application pads, in fluid flow contact with the strip, which function to regulate the flow of test sample to the chromatographic material, to filter the test samples and to deliver and/or mix assay reagents. Assay reagents may be incorporated within the application pad as well as in the chromatographic material. By varying the configuration of reagent-containing sites on the device, qualitative and quantitative displays of assay results can be obtained. Preferably, the reagents are situated in the devices in such a way as to make the assay substantially self-performing and to facilitate the detection and quantitation of the assay results. One or more detectable signals resulting from the reactions at the reagent-containing sites and/or the binding assay can then be detected by instrumentation or direct visual observation.

In one embodiment, the present invention is particularly advantageous in that it combines several elements to form a novel assay device with which a one-step assay can be performed for a number of different patient samples at one time. The novel device simplifies the assay protocols by decreasing the number of manual steps required for its use, thereby reducing the risk of errors during use. The combination of elements in the present invention also enables the use of predetermined amounts of reagents incorporated within the device, thereby avoiding the need for reagent measurements and additions by the user.

The present invention provides one or more control means for verifying an assay result. One control means comprises a confirmatory assay that is performed essentially automatically and simultaneously with the assay for the detection of analyte. In a particular embodiment, in which the confirmatory assay operates in a sandwich format, the test sample suspected of containing the analyte (for example, antigen Ag) is contacted with a predetermined amount of labeled reagent (in this example, antibody Ab*) to form a reaction mixture containing an analyte/labeled reagent complex (Ag-Ab*). The labeled reagent (Ab*) may be separate from or preferably incorporated within the test device. The resulting reaction mixture, migrates through the teststrip. In a first pathway, the reaction mixture contacts a patient capture site containing an immobilized anti-analyte specific binding member (I-Ab) that binds at a site on the analyte distinct from the labeled reagent. The patient capture reagent is therefore capable of binding to the Ag-Ab* complex to form an immobilized I-Ab-Ag-Ab* complex that is detectable at the patient capture site. In a second pathway, the reaction mixture first contacts a reagent zone containing a positive control reagent (Ag'). The positive control reagent (Ag') is a mobile specific binding member having the same binding specificity for the labeled reagent (Ab*) as the test analyte of interest (Ag). The positive control reagent (Ag') can be either an analyte identical to that of the test sample or a corresponding analyteanalog. When the reaction mixture contacts the positive control reagent zone, the positive control reagent (Ag') is reconstituted and binds specifically with unbound labeled reagent (Ab*) to form a positive control reagent/labeled reagent complex (Ag'-Ab*). This complex (Ag'-Ab*) migrates to the positive control capture site. The positive control capture reagent (I-Ab) located at the positive control capture site is the same reagent as immobilized at the patient capture site. Therefore, the positive control capture reagent is capable of specifically binding to the Ag'-Ab* complex to form a detectable immobilized complex (I-Ab-Ag'-Ab*). A detectable signal at the positive control capture site confirms that the assay reagents are functional and the test result valid. For example, when no analyte is present in a test sample, the negative result of the patient sample is confirmed as a valid test result when the positive control capture site has a detectable signal and the patient capture site has no detectable signal. When analyte is present in a test sample, the positive result of the patient sample is confirmed as a valid test result when the positive control capture site has a detectable signal and the patient capture site has detectable signal. No detectable signal at the positive control capture site itself, indicates either that the labeling system's reagents have degraded or that other factors in the test sample have interfered with the binding of the labeled reagent to the positive control reagent or with the binding of the labeled positive control complex to the reagent located at the positive control capture site.

Another embodiment of the present invention involves a device, having in addition to a positive control capture reagent, a negative control reagent immobilized at a site in either a first or a second pathway on the teststrip. The negative control reaagent comprises a substance that is used to indicate the presence of non-specific binding or aggregation of any labeled reagent or labeled complex in the device. In a preferred embodiment, the negative binding reagent is normal (i.e. nonimmune) antibody from the same animal source as the patient/positive control capture reagent. Since the labeled reagents of the device are specifically designed to bind only to capture reagents, either directly or indirectly (i.e. via analyte), the binding of any labeled reagent or labeled complex to the negative binding reagent should not occur. Thus the production of a detectable signal at the negative control site is indicative of an invalid test. Only the lack of a detectable signal in the negative control site confirms the absence of nonspecific binding or aggregation of reagents.

Referring now to FIG. 1, a test strip is shown which shows a preferred configuration for the location of control sites. The strip has a single fluid flow pathway formed from a piece of porous material. The application pad (1) is located at the proximal end (2) of the strip (3). The patient capture site (4) is an immobilized patient capture reagent distributed as a bar which traverses a portion of the length of the chromatographic material. The positive control capture site (5) contains an immobilized positive control capture reagent distributed as a bar in a location directly dowristream from the site of the positive control reagent (6) The positive control reagent (6) is applied as a bar approximately 0.9 mm upstream from but in the same fluid flow path as the positive control capture site (5). The procedural control site (7) contains an immobilized reagent distributed as a bar so as to form a "x" sign with the patient capture reagent. The negative control reagent (8) is applied as a bar adjacent to the "x" sign but on the opposite side of the "x" sign as the positive control capture site (5).

FIGS. 2a, 2b and 2c show alternative preferred configurations for a strip with control bars. Identical numbers refer to the identical reagents indicated in FIG. 1.

The following examples are given by way of illustration only and should not be construed as limiting the scope of the invention as based upon this disclosure. Many variations on the present invention will become obvious to those of ordinary skill in the art.

EXAMPLES

Example 1

One Step Immunochromatographic Assay For Group A Streptococcus Polysaccharide (Strep A) With Mobile Control Bars a) Labeled Reagent Preparation—Selenium Colloid/antibody Conjugates A selenium colloid suspension is prepared substantially as follows: $SeO_2$ is dissolved in water to a concentration of 0.0625 gms/mL. Ascorbate is dissolved in water to a concentration of 0.32 gms/mL and heated in a 70° C. water bath for 24 hours. The ascorbate solution is then diluted to 0.0065 gms/mL in water. The $SeO_2$ solution is quickly added to the diluted ascorbate solution and incubated at 42° C. Incubation is ended after a minimum of 42 hours when the absorbance maximum exceeds 30 at a wavelength between 542 nm and 588 nm. The colloid suspension is cooled to 2–8° C., then stored.

Selenium colloid/antibody conjugates are prepared substantially as follows: The colloid suspension is concentrated to an absorbance of 80 by centrifugation. An equal volume of either horse (or other species of antibody) (50 μg/mL) or rabbit anti-Strep A antibody (30 μg/mL) is added to the selenium colloid suspension. Both suspensions are gently mixed for about 75 minutes. 1% (by weight) bovine serum albumin (BSA) is then added at a 1:1 ratio to the antibody-:colloid conjugate mixture prior to storage at 2–8° C. A blended horse (or other species of antibody)/rabbit anti-Strep A conjugate is prepared by combining the two conjugates and diluting to an appropriate level with conjugate diluent (1% casein (by weight), 3% lactose (by weight) in 10 mM Tris, pH 7.6).

b) Application Pad Preparation

The application pad material comprises resin bonded glass fiber paper (Lydall). Approximately 0.1 ml of the blended conjugate (described in the preceding paragraph) is applied to the application pad.

c) Chromatographic Material Preparation

All reagents are applied to a nitrocellulose membrane by charge and deflect reagent jetting. The nitrocellulose is supported by a MYLAR® membrane that is coated with a pressure sensitive adhesive.

1. The patient capture/positive control capture reagent is prepared by diluting sheep anti-Strep A polyclonal antibody to a concentration of 0.5 mg/mL in jetting diluent (800 mM Tris, pH 7.6 with 2% sucrose (by weight), 0.1% BSA (by weight) and 5 μg/mL fluorescein). 0.098 μL of this capture reagent is applied to the strip in a first pathway so as to form one segment of a "x" sign and constitutes the patient capture site. 0.03 μL of this capture reagent is applied to the strip in a second pathway, adjacent to the patient capture site and downstream of the positive control reagent (APS, see below) and constitutes the positive control capture site.

2. Positive control reagent is prepared as a solution of 50 μg/mL APS (Group A Streptococcus polysaccharide) diluted in the conjugate diluent described above. 0.083 μL of positive control reagent is applied in a position approximately 0.9 mm upstream from but in the same fluid flow path as the positive control capture reagent.

3. Procedural control reagent is prepared as a solution of 0.3 mg/mL goat anti-horse polyclonal antibody in jetting diluent. 0.129 μL of procedural control reagent is applied so as to form the second segment of a "x" sign, with the first segment being the patient capture reagent.

4. Negative control reagent is prepared as a solution of 0.5 mg/mL sheep IgG in jetting diluent. 0.013 μL of negative control reagent is applied at a location adjacent to the "x" sign formed from the patient capture site and procedural control site but is located on the side of the "x" sign directly opposite of the positive control capture site.

d) Assay Protocol

A throat swab suspected of containing Strep A is first subjected to a nitrous acid extraction and the extracted sample then transferred to the test strip. The test sample passes through the application pad thereby reconstituting the selenium colloid/anti-Strep A antibody labeled reagent. If Strep A is present in the test sample, then a selenium colloid/anti-Strep A antibody/analyte complex is formed and migrates through the strip. The complex is immobilized at the patient antibody capture site where the formation of a "sandwich" immunocomplex is detected by the appearance of a visible signal.

During the course of the assay, selenium colloid/anti-Strep A antibody migrates from the application pad through the test strip and contacts the positive control reagent site, reconstituting the positive control reagent, Group A Streptococcus polysaccharide. A selenium colloid/anti-Strep A antibody/Group A Streptococcus polysaccharide complex is formed which migrates through the strip. This complex is immobilized at the positive control capture site where the formation of a "sandwich" immunocomplex is also detected by the appearance of a visible signal.

Example 2

One Step Immunochromatographic Assay For hCG With Mobile Control Bars a) Labeled Reagent Preparation—Selenium Colloid/anti-hCG Antibody Conjugate A selenium colloid suspension is prepared essentially as described in Example 1 with the exception that the $SeO_2$/ascorbate solution is incubated at 42° C. for 24 rather than 42 hours.

Selenium colloid/anti-hCG antibody conjugates are prepared substantially as follows: The colloid suspension is concentrated to an absorbance of 25 by centrifugation. Mouse anti-hCG antibody (30 μg/mL) is added to the selenium colloid suspension and the mixture is stirred for about 40 minutes. BSA is then added to the antibody:colloid conjugate mixture to a final concentration of 0.5% and stirred for 15 minutes at room temperature. The resulting selenium colloid/anti-hCG antibody conjugate is centrifuged (at 1900×g) for 40 minutes. The supernatant is removed and the concentration determined by OD.

b) Application Pad Preparation

The application pad is prepared in a manner essentially identical to that in Example 1, with the exception that the selenium colloid/mouse anti-hCG IgG suspension is diluted in a protein base diluent composed of 0.5% (by weight) casein, 2% (by weight) lactose, 1% (by volume) normal mouse serum and 1 mg/mL goat IgG in 50 mM Bis-Tris, pH 6.5. Indicator reagent is then coated onto the application material and the pad is dried.

c) Chromatographic Material Preparation

As in Example 1, all reagents are applied to a nitrocellulose membrane by charge and deflect reagent jetting. The nitrocellulose is supported by a MYLAR® membrane that is coated with a pressure sensitive adhesive.

1. The patient capture/positive control capture reagent is prepared by diluting goat anti-beta hCG polyclonal antibody (Fab IgG) to a concentration of 2.0 mg/mL in diluent comprised of 100 mM Tris-saline, pH 7.8 with 1% sucrose (by weight), and 5 μg/mL fluorescein. 0.099 μL of capture reagent is applied in a first pathway so as to form one segment of a "x" sign and constitutes the patient capture site. 0.03 μL of capture reagent is applied in a second pathway, adjacent to the patient capture site and downstream of the positive control reagent (hCG, see below). The capture reagent applied at the second site, constitutes the positive control capture site.

2. Positive control reagent is prepared as a solution of 250,000 mIU/mL hCG and 1.4 mg/mL non-immune goat IgG diluted in the same diluent as the patient capture/positive control capture reagent. 0.083 µL of positive control reagent is applied in a position approximately 1.0 mm upstream from but in the same fluid flow path as the positive control capture site.

3. Procedural control reagent is prepared as a mixture of goat anti-mouse IgG polyclonal antibody and goat anti-beta hCG polyclonal antibody (whole molecule IgG) to a concentration of 0.4 mg/mL in the same diluent as the patient capture/positive control capture reagent. 0.117 µL of procedural control reagent is applied to form the second segment of a "x" sign, with the first segment being the patient capture reagent.

4. Negative control reagent is prepared as a solution of 2 mg/mL goat IgG in the same diluent as the patient capture/positive control capture reagent. 0.014 µL of negative control reagent is applied in the same fluid flow path as the positive control reagent and capture site, but directly upstream from the positive control reagent.

d) Assay Protocol

Two to five drops (approximately 50 µL=1 drop) of a sample (urine or serum) suspected of containing hCG is contacted to the glass fiber conjugate pad. The test sample passes through the pad thereby reconstituting the selenium colloid/anti-hCG antibody labeled reagent. If hCG is present in the test sample, then a selenium colloid/anti-hCG antibody/hCG complex is formed and migrates through the strip. The complex is immobilized at the patient antibody capture site where the formation of a "sandwich" immunocomplex is detected by the appearance of a visible signal.

During the course of the assay, selenium colloid/anti-hCG antibody migrates from the application pad through the test strip and contacts the positive control reagent site, reconstituting the positive control reagent, hCG. A selenium colloid/anti-hCG antibody/hCG complex is formed which migrates through the strip. This complex is immobilized at the positive control capture site where the formation of a "sandwich" immunocomplex is also detected by the appearance of a visible signal.

The concepts of the present invention are applicable to various types of chemical and binding assays. It will be appreciated, however, that one skilled in the art can conceive of many other assays, including assays for analytes other than antigens or antibodies, to which the present inventive concepts can be applied. The embodiments described and the alternative embodiments presented are intended as examples rather than as limitations. Thus, the description of the invention is not intended to limit the invention to the particular embodiments disclosed, but it is intended to encompass all equivalents and subject matter within the scope of the invention as described above and as set forth in the following claims.

What is claimed is:

1. In an analytical device for determining the presence or amount of an analyte in a test sample, having a strip with a proximal end and a distal end, wherein the test sample can travel from said proximal end to about said distal end by capillary action, and wherein said strip contains an immobilized patient capture reagent which binds to a member selected from the group consisting of the analyte, an ancillary specific binding member and a labeled reagent, the improvement comprising:
a) a mobile positive control reagent;
b) an immobilized positive control capture reagent that is located at a site downstream from the mobile positive control reagent and is capable of binding the mobile positive control reagent.

2. The device according to claim 1, wherein the mobile positive control reagent is human chorionic gonadotropin or Group A Streptococcus polysaccharide.

3. The device according to claim 1, wherein said immobilized positive control capture reagent is configured as a letter, number, icon, or symbol.

4. The device according to claim 3 wherein the immobilized positive control capture reagent is located adjacent the immobilized patient capture reagent.

5. The device according to claim 1, further comprising an immobilized negative control reagent used to determine the presence of non-specific binding or aggregation of any labeled reagent in the device.

6. The device according to claim 5, wherein the immobilized negative control reagent is non-immune antibody prepared from the same or a different animal source as the patient capture reagent.

7. The device according to claim 5 wherein the negative control reagent is located adjacent the immobilized patient capture reagent.

8. The device according to claim 7 wherein the negative control reagent is configured as a letter, number, icon, or symbol.

9. The device according to claim 1, wherein a labeled reagent is contained within the strip in a situs between the proximal end and the immobilized patient capture reagent.

10. The device according to claim 9, wherein the positive control capture reagent is an immobilized anti-Group A Streptococcus antibody and the labeled reagent is a labeled anti-Group A Streptococcus antibody.

11. The device according to claim 9, wherein the positive control capture reagent is an immobilized anti-human chorionic gonadotropin antibody and the labeled reagent is a labeled anti-human chorionic gonadotropin antibody.

12. A kit for use in specific binding assays, having an analytical device for determining the presence or amount of an analyte in a test sample, comprising a strip having a proximal end and a distal end, wherein the test sample can travel from said proximal end to about said distal end by capillary action, and wherein said strip contains an immobilized patient capture reagent which binds to a member selected from the group consisting of the analyte, an ancillary specific binding member and a labeled reagent, the improvement comprising:
a) a mobile positive control reagent;
b) an immobilized positive control capture reagent that is located at a site downstream from the mobile positive control reagent and is capable of binding the mobile positive control reagent.

13. The kit according to claim 12, further comprising an immobilized negative control reagent used to determine the presence of non-specific binding or aggregation of any labeled reagent in the device.

* * * * *